United States Patent [19]

Petitou et al.

[11] Patent Number: 5,773,605
[45] Date of Patent: Jun. 30, 1998

[54] SULFATED GLYCOSAMINOGLYCANOID DERIVATIVES OF THE HEPARIN SULFATE TYPE

[75] Inventors: Maurice Petitou, Paris, France; Constant Adriaan Anton van Boeckel, Oss, Netherlands

[73] Assignee: Akzo Nobel N.V., Arnhem, Netherlands

[21] Appl. No.: 652,737

[22] Filed: May 23, 1996

Related U.S. Application Data

[63] Continuation of Ser. No. 333,448, Nov. 2, 1994, Pat. No. 5,529,985, which is a continuation of Ser. No. 325,841, Oct. 19, 1994, Pat. No. 5,543,403, which is a continuation-in-part of Ser. No. 795,595, Nov. 21, 1991, abandoned, which is a continuation-in-part of Ser. No. 690,035, Apr. 23, 1991, abandoned.

[30] Foreign Application Priority Data

Aug. 23, 1990 [EP] European Pat. Off. ............. 90201006

[51] Int. Cl.⁶ ..................... C07H 11/00; C07H 13/02; C07H 1/00
[52] U.S. Cl. ................. 536/118; 536/21; 536/53; 536/119; 536/122; 536/124
[58] Field of Search ............... 536/21, 118, 122, 536/53, 119, 124

[56] References Cited

U.S. PATENT DOCUMENTS

| | | | |
|---|---|---|---|
| 3,301,848 | 1/1967 | Halleck | 536/118 |
| 4,105,760 | 8/1978 | Szejtli et al. | 536/118 |
| 4,221,907 | 9/1980 | Nair et al. | 536/118 |
| 4,699,900 | 10/1987 | Bayol et al. | 514/54 |
| 4,713,373 | 12/1987 | Bayol et al. | 514/54 |
| 4,818,816 | 4/1989 | Petitou et al. | 536/118 |
| 4,841,041 | 6/1989 | van Boeckel et al. | 536/118 |
| 5,380,716 | 1/1995 | Conrad et al. | 536/21 |

*Primary Examiner*—John Kight
*Assistant Examiner*—Everett White
*Attorney, Agent, or Firm*—Mary E. Gormley

[57] ABSTRACT

The invention relates to sulfated glycosaminoglycanoid derivatives of the heparin and heparan sulfate type, of which N-sulfate, N-acetate, and hydroxy groups, are replaced by alkoxy, aryloxy, aralkoxy, or O-sulfate groups. The compounds have antithrombotic and smooth muscle cell proliferation inhibiting activities.

1 Claim, No Drawings

SULFATED GLYCOSAMINOGLYCANOID DERIVATIVES OF THE HEPARIN SULFATE TYPE

This application is a continuation of application Ser. No. 08/333,448 filed Nov. 2, 1994, now U.S. Pat. No. 5,529,985, which is a continuation of application Ser. No. 08/325,841 filed Oct. 19, 1994, now U.S. Pat. No. 5,543,403, which is a Continuation-in-part of application Ser. No. 07/795,595 filed Nov. 21, 1991, now abandoned, which is a Continuation-in-part of 07/690,035 filed Apr. 3, 1991, now abandoned.

The invention concerns a sulfated glycosaminoglycanoid derivative of the heparin and heparan sulfate type, of which N-sulfate, N-acetate, and hydroxy groups, are replaced by alkoxy, aryloxy, aralkoxy, or O-sulfate groups. The invention is further related to a process for the preparation of said derivative, a pharmaceutical composition containing the same, and a method of treatment using said derivatives.

Sulfated glycosaminoglycan derivatives are known. European patent EP 84,999, for instance, discloses sulfated pentasaccharides of the chemical class of glycosaminoglycans having antithrombotic activity. These known compounds can possess, apart from hydroxy groups, O-sulfate, N-sulfate, and N-acetyl groups, whereas the anomeric hydroxy group is sometimes replaced by a methoxy group.

In contrast to the known compounds, the present sulfated glycosaminoglycanoid derivatives do not have free hydroxy groups, nor do they possess N-sulfate or N-acetate groups.

It has now been found that the compounds of this invention have a better binding affinity to antithrombin III with respect to the naturally occuring pentasaccharide of European patent EP 84,999, which results in a better pharmacokinetic profile, longer half-life times, and lower therapeutic doses and thus lesser side-effects. Furthermore, the compounds of this invention have a substantially better heparin cofactor II.(HCII) mediated antithrombin activity; and are, therefore, more effective as thrombin generation inhibitors than the prior art compounds. The sulfated glycosaminoglycanoid derivatives can also be used as inhibitors for smooth muscle cell proliferation, and for the treatment of angiogenesis, cancer, and retrovirus infections, like HIV.

The inclusion of alkyl, aryl, or aralkyl functionalized saccharide units gives further a very important synthetic advantage over the prior art compounds. By functionalizing the hydroxy groups with alkyl, aryl, or aralkyl groups, it is in most cases redundant to prepare temporarily protected carbohydrates, which makes the synthetic pathway considerably shorter and simpler, whereas the replacement of the glucosamine units by glucose units further simplifies the synthesis of the saccharides significantly. Moreover, an additional advantage of the synthesis of the compounds of the invention is that the nature of the temporarily protective groups, which are necessary for the protection of the hydroxy groups to be sulfated, is not critical.

More specifically, the compounds according to this invention are sulfated glycosaminoglycanoid derivatives, comprising the saccharide unit having the formula I or II

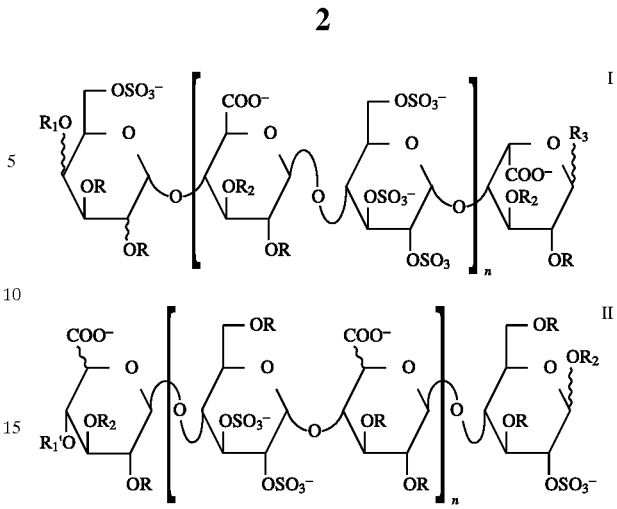

in which the twitched lines denote an a or B bond, each of the groups R are independently selected from the group consisting of alkyl and sulfate; n is 1 or 2; $R_1$ is alkyl, aryl, or aralkyl; and $R_1'$ has the same meaning as R, or is aryl, aralkyl or

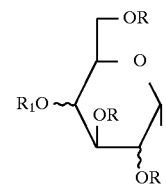

wherein R, $R_1$, and the twitched lines have the previously given meanings; $R_2$ is alkyl; and $R_3$ is alkoxy, or

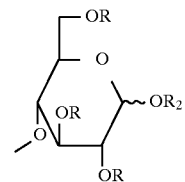

wherein the twitched line, R and R2 have the previously given meanings, and the charged moieties are compensated by counter-ions.

Preferred compounds have the tetrasaccharide unit of the general formula III

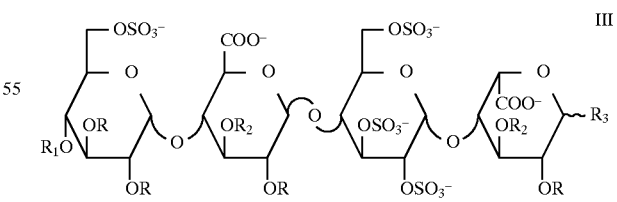

wherein the twitched line, R, $R_1$, $R_2$, and $R_3$ have the
previously given meanings; and the charged moieties are compensated by counter-ions.

A very suitable derivative III has the structure:

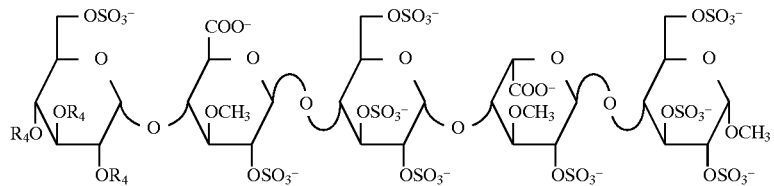

wherein $R_4$ is independently methyl or $SO_3^-$.

The alkyl group in the definition of R, $R_1$, $R_1'$, and $R_2$ is a branched or unbranched alkyl group having 1–8 carbon atoms or a cyclo-alkyl group having 3–8 carbon atoms. Alkyl groups for different groups R or R2 may be different. Examples are methyl, ethyl, isopropyl, butyl, sec-butyl, pentyl, neopentyl, hexyl, and octyl. Preferred are the alkyl groups having 1–6 carbon atoms. More preferred are the alkyl groups having 1–4 carbon atoms, and most preferred is a methyl group.

The term aryl in the definition of $R_1$ and $R_1'$ means an aromatic group, preferably phenyl, which may be substituted by OH, alkyl having 1–4 carbon atoms, alkoxy having 1–4 carbon atoms, halogen (preferably fluorine, chlorine, or bromine), $CF_3$, or NR'R", wherein R'and R"are independently hydrogen or alkyl having 1–4 carbon atoms, or R'is $SO_3^-$ and R" is hydrogen.

The term aralkyl means an aralkyl group in which the alkyl moiety is an alkyl group having 1–4 carbon atoms and the aryl moiety is an aryl group as previously defined.

In the term alkoxy, used in the definitions of $R_3$ the alkyl moiety has the same meaning as given previously for the alkyl group.

The term "α or B" means that the configuration of the concerned bond is respectively trans or cis with respect to the anomeric bond in the concerned saccharide unit, or when it concerns the anomeric bond itself, it has the usual meaning of carbohydrate chemistry.

The term sulfated glycosaminoglycanoid derivative means a sulfated glycosaminoglycan derivative, in which the N-sulfate group(s) is (are) replaced by alkoxy, and preferably by O-sulfate groups. A glycosaminoglycan is a carbohydrate which belongs to the well-known chemical class of glycosaminoglycans.

Preferred compounds have R and $R_1$ is alkyl, and more preferably methyl, at sites where the corresponding naturally occurring glycosaminoglycans possess a free hydroxy group or an acetamido group, and $R_1'$ and $R_3$ are the monosaccharide units as indicated in the meanings of formulae I and II.

It is generally believed that multipoint key polar interactions are of essential importance throughout molecular biology for ensuring high selectivity in non-covalent molecular associations, and that substitution of only one of the key hydroxy groups of an oligosaccharide by a hydrophobic group (and invariably a number of the hydroxy groups prove outstandingly essential to complex formation) can result in complete loss of the affinity by the protein. Remarkably, however, the preferred compounds of this invention having O-alkyl and O-sulfate groups without having free hydroxy groups, still show the full-blown activity.

The counter-ions which compensate the charged moieties are pharmaceutically acceptable counter-ions, like hydrogen, or more preferably alkali or earth-alkali metal ions, like sodium; calcium, or magnesium.

The carbohydrates according to this invention may be prepared according to well known methods described and used for the synthesis of polysaccharides. In this respect, particular reference is made to the previously mentioned European patent EP 84,999, in which methods for the synthesis of polysaccharides are disclosed.

A suitable process for the preparation of the sulfated glycosaminoglycanoid derivative of this invention is characterized in that protected monosaccharides are coupled to give protected disaccharides, which are optionally further coupled to tetra-, penta- or hexa-saccharides, after which the protective groups are partially or completely cleaved and free hydroxy groups are sulfated, after which, if present, remaining protective groups are cleaved, and the compound obtained is optionally converted into a pharmaceutically acceptable salt.

A stepwise condensation of the monosaccharides is possible. In general, however, building blocks consisting of D-glucose, L-idose, D-glucuronic acid or L-iduronic acid, suitably functionalized with the required alkyl, aryl, or aralkyl groups or by temporarily protective groups, are condensed together in the desired order. In this way the (protected) saccharide unit can be prepared, which can be coupled with other saccharide units, or protected derivatives thereof. Suitable protective groups are well known in carbohydrate chemistry. Preferred protective groups include benzyl and acetyl for hydroxy groups, and methyl and benzyl for the carboxylate group of uronic acids. Other protective groups like levulinoyl, chloroacetyl, trityl, benzoyl, and the like, may be used with equal success. Coupling of the saccharides is performed in a manner known in the art, e.g. deprotection of the I-position of the glycosyl-donor, and/or activation of this position (e.g. by making a bromide, pentenyl, fluoride, thioglycoside, or trichloroacetamide derivative) and coupling the activated glycosyl-donor with an optionally protected glycosylacceptor.

This process of stepwise or building block synthesis affords for example a protected carbohydrate derivative comprising a tetrasaccharide unit of the general formulae I or II, but having protective groups at the positions where sulfate groups are attached. The protective groups are hydroxy protective group (preferably benzyl or acetyl). The protected carbohydrate derivative can be deprotected and sulfated in a manner as described in the previously mentioned EP 84,999 in order to obtain the carbohydrate derivative according to formulae I and II. Suitable deprotection methods are, for example, basic hydrolysis for acetyland methyl-esters, and hydrogenolysis for benzyl ethers. Sulfation can successfully be performed with complexes of sulfur trioxide with bases like trimethylamine, triethylamine or pyridine in a suitable solvent.

For the treatment of venous thrombosis or for the inhibition of smooth muscle cell proliferation the compounds of the invention may be administered enterally or parenterally, and for humans preferably in a daily dosage of 0.001–10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1 methyl O-4-O-(4-sulfoaminophenyl)-2,3,6 -tri-O-sulfo-α-D-glucopyranosyl-(1→4)-O-3-O-methyl-2 -O-sulfo-α-L-ido-pyranuronosyl-(1→4 )-O-2,3,6-tri-O-sulfo-α-D-glucopyran-oside nonakis sodium salt.

Methyl O-4-O-(4-nitrophenyl)-6-O-acetyl-2,3-O-di-phenyl-methyl-α-D-glucopyranosyl-(1-4)-Q-(methyl 3-O-methyl-2-O-acetyl-α-L-idopyranosyluronate)-(1→4)-O-2,3,6-tri-O-acetyl-α-D-glucopyranoside (100 mg, 0.09 mmol), obtained by the known imidate coupling of the trichloroacetimidate of O-4-O-(4-nitrophenyl)-6-O-acetyl-2,3-O-di-phenylmethyl-α-D-glucopyranoside and methyl O-(methyl 3-O-methyl-2-O-acetyl-α-L-idopyranosyluronate)-(1→4)-O-2,3,6-tri-O-acetyl-α-D-glucopyranoside, was dissolved in tetrahydrofuran (9 ml) and cooled to −5° C. At this temperature a 30% aquous solution of hydrogen peroxide (4.5 ml) was added to the reaction mixture, and after 10 min a 1.25 M lithium hydroxide solution (4.7 ml) was added. The mixture was stirred for 1 h at −5° C., after which time the temperature was raised to 0° C. and the mixture was stirred overnight. The reaction mixture was acidified with 6N hydrogen chloride at 0° C. to pH 1.5, after which the saponified compound was extracted with ethyl acetate. The organic layers were pooled, dried over magnesium sulfate, and evaporated to give 63 mg (84%) of methyl O-4-O-(4-nitrophenyl)-2,3-O-di-phenyl-methyl-α-D-glucopyranosyl-(1→4)-O-3-O-methyl-α-L-ido-pyranuronosyl-(1→4)-O-α-D-glucopyranoside, which was dissolved in 8 ml of methanol. 10% Pd on charcoal (63 mg) was added and the mixture hydrogenolyzed overnight. After filtration and evaporation 27 mg (50%) of methyl O-4-O-(4-aminophenyl)-α-D-glucopyranosyl-(1→4)-O-3-O-methyl-α-L-idopyranuronosyl-(1→4)-O-α-D-glucopyranoside were obtained.

13 mg of methyl O-4-O-(4-aminophenyl)-O-α-D-glucopyranosyl-(1→4)-O-3-O-methyl-α-L-idopyranuronosyl-(1→4)-O-α-D-glucopyranoside were dissolved in 2 ml of dry N,N-dimethylformamide, and under an atmosphere of nitrogen 148 mg of triethylamine sulfurtrioxide complex were added. The mixture was stirred overnight at 50° C., after which an aquous solution of sodium hydrogen carbonate was added under ice cooling. The mixture was stirred for 1 h at room temperature, concentrated to a small volume and desalted on a Sephadex G-10 column with water. The crude product obtained was purified by HPLC using a Mono-Q anion exchange column to give 11 mg (37%) of methyl O-4-O-(4-sulfoaminophenyl)-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside nonakis sodium salt. $[\alpha]_D^{20}$=+52.2° (c=0.67; water). Anomeric protons chemical shifts: 5.5; 5.17; and 5.15 ppm.

EXAMPLE 2

In a similar way as described in the example 1 were prepared:

methyl O-3,4-di-O-methyl-2,6-di-O-sulfo-α-D-glucopyranosyl-(1→4)-O-2,3-di-O-methyl-e-L-idopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside undecakis sodium salt. $[\alpha]D^{20}$ =+26.5° (c=0.46; water). Anomeric protons chemical shifts: 5.56; 5.39; 5.31; 5.14; and 5.13 ppm. methyl O-2,3,4-tri-O-methyl-6-O-sulfo-α-D-glucopyranosyl-(1→4)-O-2, 3-di-O-methyl-β-D-glucopyranuronosyl-(1→4)-O-2,3,6-tri-O-sulfo-α-D-glucopyranosyl-(1→4)-O-2,3-di-O-methyl-α-L-idopyranuronosyl-(1→4)-O-2,3,6-tri-O-sulfo-α-D-glucopyranoside nonakis sodium salt. $[\alpha]_D^{20}$=+55° (c=1; water). Anomeric protons chemical shifts: 5.47; 5.42; 5.17; 5.14; and 4.67 ppm.

methyl O-3,4-di-O-methyl-2,6-di-O-sulfo-α-D-glucopyranosyl-(1→4)-O-2,3-di-O-methyl-β-D-glucopyranuronosyl-(1→4)-O-2,3,6-tri-o-sulfo-α-D-glucopyranosyl-(1→4)-O-2,3-di-O-methyl-α-L-idopyranuronosyl-(1→4)-O-2,3,6-tri-O-sulfo-α-D-glucopyranoside decakis sodium salt. $[\alpha]_D^{20}$ =+53° (c=1; water). Anomeric protons chemical shifts: 5.56; 5.45; 5.19; 4.81; and 4.70 ppm.

methyl O-4-O-methyl-2,3,6-tri-O-sulfo-α-D-glucopyranosyl-(1→4)-O-2, 3-di-O-methyl-b-D-glucopyranuronosyl-(1→4)-O-2, 3,6-tri-O-sulfo-α-D-glucopyranosyl-(14)-O-2,3-di-O-methyl-α-L-idopyranuronosyl-(1→4)-O-2, 3,6-tri-O-sulfo-α-D-glucopyranoside undecakis sodium salt. $[\alpha]_D^{20}$=+47.5° (c=1; water). Anomeric protons chemical shifts: 5.60; 5.42; 5.16; 5.09; and 4.66 ppm.

methyl O-2,3,4-tri-O-methyl-6-O-sulfo-α-D-glucopyranosyl-(1→4)-O-2,3-di-O-methyl-α-L-idopyranuronosyl-(14)-O-2,3,6-tri-O-sulfo-α-D-glucopyranosyl-(1→4)-O-2,3-O-di-methyl-α-L-idopyranuronosyl-(1→4)-O-2,3,6-tri-O-sulfo-α-D-glucopyranoside nonakis sodium salt. $[\alpha]_D^{20}$ =+46.2° (c=1; water). Anomeric protons chemical shifts: 5.43; 5.37; 5.16; 5.09; and 5.09 ppm.

methyl O-2,3,4-tri-O-methyl-6-O-sulfo-α-D-glucopyranosyl-(1→4) -O-3-O-methyl-2-O-sulfo-β-D-glucopyranuronosyl-(1→4) -O-2, 3,6-tri-O-sulfo-α-D-glucopyranosyl-(1→4)-O-3-O-methyl-2-o-sulfo-α-L-idopyranuronosyl-(1→4)-O-2,3,6-tri-O-sulfo-α-D-glucopyranoside undecakis sodium salt. $[\alpha]_D^{20}$=+46.7° (c=0.55; water). Anomeric protons chemical shifts: 5.49; 5.48; 5.16; 5.15; and 4.76 ppm.

methyl O-4-O-methyl-2,3,6-tri-O-sulfo-α-D-glucopyranosyl-(1→4)-O-3-O-methyl-2-O-sulfo-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-e-D-glucopyranoside tridecakis sodium salt. $[\alpha]_D^{20}$=+42.2+ (c=1; water). Anomeric protons chemical shifts: 5.61; 5.48; 5.15; 4.86; and 4.76 ppm.

methyl O-3,4-di-O-methyl-2,6-di-O-sulfo-α-D-glucopyranosyl-(1→4)-O-2,3-di-O-methyl-α-L-idopyranuronosyl-(1→4)-O-2,3,6-tri-O-sulfo-α-D-glucopyranosyl-(1→4)-O-2,3-di-O-methyl-α-L-idopyranuronosyl-(1→4)-O-2,3,6-tri-O-sulfo-α-D-glucopyranoside decakis sodium salt. $[\alpha]_D^{20}$=+42.2 (c=1; water).

methyl O-2-O-methyl-3,4,6-tri-O-sulfo-α-D-glucopyranosyl-(1→4)-O-3-O-methyl-2-O-sulfo-β-D- glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside tridecakis sodium salt.

methyl O-2,3-di-O-methyl-4,6-di-O-sulfo-α-D-glucopyranosyl-(1→4)-O-3-O-methyl-2-O-sulfo-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside dodecakis sodium salt. methyl O-2,4-di-O-methyl-3,6-di-O-sulfo-α-D-glucopyranosyl-(1→4)-O-3-O-methyl-2-O-sulfo-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside dodecakis sodium salt.

methyl O-4-O-methyl-2,3,6-tri-O-sulfo-α-D-mannopyranosyl-(1→4)-O-2,3-di-O-methyl-β-D-glucopyranuronosyl-(1→4)-O-2,3,6-tri-O-sulfo-α-D-glucopyranosyl-(1→4)-O-2,3-di-O-methyl-α-L-idopyranuronosyl-(1→4)-O-2,3,6-tri-O-sulfo-α-D-glucopyranoside undecakis sodium salt.

methyl O-2,3,4-tri-O-methyl-α-D-glucopyranosyl-(1→4)-O-3-O-methyl-2-O-sulfo-α-L-idopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranosyl undecakis sodium salt.

methyl O-2,3-di-O-methyl-4-O-sulfo-α-L-idopyranuronosyl-(1→4)-O-2,3,6-tri-O-sulfo-α-D-glucopyranosyl-(1 →4)-O-2,3-di-O-methyl-α-L-idopyranuronosyl-(1→4)-O-2,3,6-tri-O-sulfo-α-D-glucopyranosyl-(1→4)-O-2,3-di-O-methyl-α-L-idopyranosyl-(1→4)-O-2,3,6-tri-O-sulfo-α-D-glucopyranoside tridecakis sodium salt. Anomeric protons chemical shifts: 5.40; 5.37; 5.10; 5.05; 5.05 ppm.

EXAMPLE 3 methyl 0-3,4-di-O-methyl-2,6-di-sulfo-α-D-glucopyranosyl-(1→4)-O-2,3-di-O-methyl-β-D-glucopyranuronosyl-1→4)-2,3,6-tri-O-sulfo-α-D-glucopyranosyl-(1→4)-O-3-O-methyl-2-O-sulfo-α-L-idopyranuronosyl-(1→4)-2,3,6-tri-O-sulfo-α-D-lucyranoside undecakis sodium salt a. methyl 6-O-acetyl-3,4-di-O-methyl-2-O-phenylmethyl-α-D-glucopyranosyl-(1→4)-O-(methyl 2,3-di-O-methyl-β-D-glucopyranosyluronate)-( 1→4)-O-3,6-di-O-acetyl-2-O-phenylmethyl-α-D-glucopyranosyl-(1→4)-O-(methyl 2-O-acetyl-3-O-methyl-α-L-idopyranosyluronate)-(1→4)-O-2,3,6-tri-O-acetyl-α-D-glucopyranoside (0.061 mmol; prepared according to the methods described in EP 84,999) was dissolved in 4.2 ml of chloroform and added to a mixture of 3 ml of chloroform, 18 ml of methanol and 3.7 ml of 4N sodium hydroxide. The mixture was stirred for 20 h at room temperature and after neutralizing with a diluted aqueous hydrochloric acid solution, evaporated to dryness. The residue was treated with methanol and the insoluble salts were filtered off. The filtrate was evaporated to dryness to obtain methyl 0-3,4-di-O-methyl-2-O-phenylmethyl-α-D-glucopyranosyl-(1→4)-O-2,3-di-O-methyl-β-D-glucopyranuronosyl-(1→4)-O-2-O-phenyl-methyl-α-D-glucopyranosyl-(1→4)-O-3-O-methyl-α-L-ido-pyranuronosyl-(1→4)-O-α-D-glucopyranoside disodium salt.

b. Crude methyl O-3,4-di-O-methyl-2-O-phenylmethyl-α-D-glucopyranosyl-(1→4)-O-2,3-di-O-methyl-β-D-glucopyranuronosyl-(1→4)-O-2-O-phenylmethyl-α-D-glucopyranosyl-(1→4)-O-3-O-methyl-α-L-idopyranuronosyl-(1→4)-O-α-D-glucopyranoside disodium salt was dissolved in a mixture of 3 ml of water and 1 ml of methanol and 50 mg of 10% Pd/C were added. The mixture was stirred under an atmosphere of hydrogen for 24 h at room temperature. After filtration the filtrate was evaporated to dryness, dissolved in water and desalted on Sephadex G-25. The combined fractions containing the pentasaccharide were evaporated to dryness to give methyl 3,4-di-O-methyl-α-D-glucopyranosyl-(1→4)-O-2,3-di-O-methyl-β-D-glucopyranuronosyl-(1→4)-O-α-D-glucopyranosyl-(1→4)-O-3-O-methyl-α-L-idopyranuronosyl-(1→4)-O-α-D-glucopyranoside disodium salt.

c. methyl O-3,4-di-O-methyl-α-D-glucopyranosyl-(1→4)-O-2,3-di-O-methyl-β-D-glucopyranuronosyl-(-1→4)-O-α-D-glucopyranosyl-(1→4)-O-3-O-methyl-α-L-idopyranuronosyl-(1→4)-O-α-D-glucopyranoside disodium salt was dissolved in a mixture of 2.5 ml of dry dimethylformamide and 1.4 mmol triethylamine sulfur trioxide complex. The mixture was stirred for 20 h at 50° C., after which the mixture was cooled to room temperature and a mixture of 500 mg of sodium hydrogen carbonate in 7 ml of water was added. The mixture was stirred for 30 min and then evaporated to dryness. The residue was dissolved in water, desalted on Sephadex G-25, after which the combined fractions were freeze-dried to give amorphous methyl O-3,4-di-O-methyl-2,6-di-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside undecakis sodium salt. $[\alpha]_D^{20}$=+51.3° (c 0.4; water). Anomeric protons chemical shifts: 4.68; 5.14; 5.25; 5.28; and 5.40 ppm.

EXAMPLE 4

In a similar manner as described in Example 3 can be prepared:

methyl O-2,3,4,6-tetra-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside tridecakis sodium salt. $[\alpha]_D^{20}$=44.5 (c=1; water). Anomeric protons chemical shifts: 4.52; 4.79; 4.97; 5.36; and 5.48 ppm.

methyl O-2,3,4,6-tetra-O-sulfo-α-D-glucopyranosyl-(1→4)-O-3-O-methyl-2-O-sulfo-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside tetradecakis sodium salt. $[\alpha]_D^{20}$=+45.1° (c=1; water). Anomeric protons chemical shifts: 4.76; 5.14; 5.15; 5.48; and 5.64 ppm.

methyl O-3,4-di-O-n-hexyl-2,6-di-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside undecakis sodium salt. $[\alpha]_D^{20}$=+40.8° (c=1; water). Anomeric protons chemical shifts: 4.68; 5.14; 5.16; 5.52; and 5.56 ppm.

methyl O-3,4-di-O-methyl-2,6-di-O-sulfo-α-D-glucopyranosyl-(1→4)-O-3-O-methyl-2-O-sulfo-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside dodecakis sodium salt. $[\alpha]_D^{20}$=+38.5 (c=1; water). Anomeric protons chemical shifts: 5.13; 5.14; 5.31; and 5.56 ppm.

methyl O-(4-aminophenyl)-2,3,6-tri-O-sulfo-α-D-glucopyranosyl-(1→4)-O-2,3-di-O-methyl-β-D- glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside dodecakis sodium salt. $[\alpha]_D^{20}$=+56.0° (c=1; water). Anomeric protons chemical shifts: 4.69; 5.14; 5.16; 5.52; and 5.65 ppm.

methyl O-(4-sulfoaminophenyl)-2,3,6-tri-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside tridecakis sodium salt. $[\alpha]_D^{20}$=+57.0 (c=1; water). Anomeric protons chemical shifts: 4.69; 5.13; 5.13; 5.53; and 5.67 ppm.

EXAMPLE 5 methyl O-3,4-di-O-methyl-2,6-di-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-octyl-2-O-sulfo-α-L-idopyranuronosyl-(1→4)-O-2,3,6-tri-O-sulfo-α-D-glucopyranoside undecakis sodium salt.

a. methyl O-6-O-acetyl-3,4-di-O-methyl-2-O-phenylmethyl-α-D-glucopyranosyl-(1→4)-O-(phenylmethyl 2,3-di-O-methyl-β-D-glucopyranuronosyluronate)-(1→4)-O-3,6-di-O-acetyl-2-O-phenylmethyl-α-D-glucopyranosyl-(1→4)-O-(phenylmethyl 2-O-benzoyl-3-O-octyl-α-L-idopyranuron-osyluronate)-(1→4)-O-2,3,6-tri-O-benzoyl-α-D-glucopyranoside (0.051 mmol) was dissolved in methanol and the catalyst (10% Pd/C) was added. The mixture was stirred under an atmosphere of hydrogen for 2 days at room temperature then, after filtration, the solvent was evaporated to dryness to give methyl O-6-O-acetyl-3,4-di-O-methyl-α-D-glucopyranosyl-(1→4)-O-2,3-di-O-methyl-β-D-glucopyranuronate-(1→4)-O-3,6-di-O-acetyl-α-D-glucopyranosyl-(1→4)-O-2-O-benzoyl-3-O-octyl-α-L-idopyranunonate-(1→4)-O-2,3,6-tri-O-benzoyl-α-D-glucopyranoside.

b. methyl O-6-O-acetyl-3,4-di-O-methyl-α-D-glucopyranosyl-(1→4)-O-2,3-di-O-methyl-β-D-glucopyranuronate-(1→4)-O-3,6-di-O-acetyl-α-D-glucopyranosyl-(1→4)-O-2-O-benzoyl-3-O-octyl-α-L-idopyranuronate)-(1→4)-O-2,3,6-tri-O-benzoyl-α-D-glucopyranoside was dissolved in methanol (8 ml) and sodium hydroxyde (5N solution) was added (0.9 ml). After 15 minutes at room temperature the solution was neutralized with Dowex-50-H$^{30}$ resin, filtered and evaporated to dryness to give methyl O-3,4-di-O-methyl-α-D-glucopyranosyl-(114)-O-2,3-di-O-methyl-β-D-glucopyranuronate-(1→4)-O-α-D-glucopyranosyl-(1→4)-O-3-O-octyl-α-L-idopyranuronate-(1→4)-O-α-D-glucopyranoside (48 mg).

c. methyl O-3,4-di-O-methyl-α-D-glucopyranosyl-(1→4)-O-2,3-di-O-methyl-β-D-glucopyranuronate-(1→4)-O-α-D-glucopyranosyl-(1→4)-O-3-O-octyl-α-L-idopyranuronate-(1→4)-O-α-D-glucopyranoside (48 mg) was dissolved in dimethylformamide (1.4 ml) and sulfur trioxidetriethylamine complex (1.8 mmol) was added. After one night at 55° C. the mixture was cooled to room temperature and a mixture of sodium hydrogen carbonate (500 mg) and water (2 ml) was added. After evaporation the residue was layered on top of a Sephadex G25 column and eluted with water. The appropriate fractions were combined and freeze dried to give methyl O-3,4-di-O-methyl-2,6-di-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-octyl-2-O-sulfo-α-L-idopyranuronosyl-(1→4)-O-2,3,6-tri-O-sulfo-α-D-glucopyranoside undecakis sodium salt. $[\alpha]_D^{20}$=+40 (c=1.2; water). Anomeric protons chemical shifts: 4.68; 5.12; 5.13; 5.52; and 5.53 ppm.

EXAMPLE 6 in a similar manner, as described in Example 5, were prepared:

methyl O-3,4-di-O-methyl-2,6-di-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-butyl-2-O-sulfo-α-L-idopyranuronosyl-(1→4)-O-2,3,6-O-sulfo-α-D-glucopyranoside undecakis sodium salt. $[\alpha]_D^{20}$=+40° (c=0.86; water).

methyl O-3,4-di-O-methyl-2,6-di-O-sulfo-α-D-glucopyranosyl-(1→4)-O-2,3-di-O-butyl-β-D-glucopyranuronosyl-(1→4)-O-2,3,6-tri-O-sulfo-α-D-glucopyranosyl-(1→4)-O-3-O-octyl-2-O-sulfo-α-L-idopyranuronosyl-(1→4)-O-2,3,6-tri-O-sulfo-α-D-glucopyranoside undecakis sodium salt. $[\alpha]_D^{20}$=+38° (c=0.95; water).

methyl O-3,4-di-O-methyl-2,6-di-O-sulfo-α-D-glucopyranosyl-(1→4)-O-2,3-di-O-butyl-β-D-glucopyranuronosyl-(1→4)-O-2,3,6-tri-O-sulfo-α-D-glucopyranosyl-(1→4)-ρ-3-O-methyl-2-O-sulfo-α-L-idopyranuronosyl-(1→4)-O-2,3,6-tri-O-sulfo-α-D-glucopyranoside undecakis sodium salt. $[\alpha]_D^{20}$=+43° (c=0.92; water).

EXAMPLE 7 methyl O-3,4-di-O-methyl-2,6-di-O-sulfo-α-D-glucopyranosyl-(1→4)-O-2,3-di-O-methyl-β-D-glucopyranuronosyl-(1→4)-O-2,3.6-tri-O-sulfo-α-D-glucopyranosyl-(1→4)-O-3-O-ethyl-2-O-sulfo-α-L-idopyranuronosyl-(1→4)-O-2,3,6-tri-O-sulfo-α-D-glucopyranoside undecakis sodium salt.

a. methyl O-6-O-acetyl-3,4-di-O-methyl-2-O-phenylmethyl-α-D-glucopyranosyl-(1→4)-O-(phenylmethyl 2,3-di-O-methyl-β-D-glucopyranuronosyluronate)-(1→4)-O-3,6-di-O-acetyl-2-O-phenylmethyl-α-D-glucopyranosyl-(1→4)-O-(phenylmethyl 2-O-benzoyl-3-O-ethyl-α-L-idopyranuronosyluronate)-(1→4)-O-2,3,6-tri-O-benzoyl-α-D-gluco-pyranoside (0.051 mmol) was dissolved in methanol and the catalyst (10% Pd/C) was added. The mixture was stirred under an atmosphere of hydrogen for 2 days at room temperature then, after filtration, the solvent was evaporated to dryness to give methyl O-6-O-acetyl- 3,4-di-O-methyl-α-D-glucopyranosyl-(1→4)-O-2,3-di-O-methyl-β-D-glucopyranuronate-(1→4)-O-3, 6-di-O-acetyl-α-D-glucopyranosyl-(1→4)-O-2-O-benzoyl-3-O-ethyl-α-L-idopyranunonate-(1→4)-O-2,3, 6-tri-O-benzoyl-α-D-glucopyranoside.

b. methyl O-6-O-acetyl-3,4-di-O-methyl-α-D-glucopyranosyl-(1→4)-O-2,3-di-O-methyl-β-D-glucopyranuronate-(1→4)-O-3,6-di-O-acetyl-α-D-glucopyranosyl-(1→4)-O-2-O-benzoyl-3-O-ethyl-α-L-idopyranuronate)-(1→4)-O-2,3,6-tri-O-benzoyl-α-D-glucopyranoside was dissolved in methanol (8 ml) and sodium hydroxyde (5N solution) was added (0.9 ml). After 15 minutes at room temperature the solution was neutralized with- Dowex-50-H$^+$ resin, filtered and evaporated to dryness to give methyl O-3,4-di-O-methyl-α-D-glucopyranosyl-(1→4)-O-2,3-di-O-methyl-β-D-glucopyranuronate-(1→4)-O-α-D-glucopyranosyl-(1→4)-O-3-O-ethyl-α-L-idopyranuronate-(1→4)-O-α-D-glucopyranoside (48 mg).

c. methyl O-3,4-di-O-methyl-α-D-glucopyranosyl-(1→4)-O-2,3-di-O-methyl-β-D-glucopyranuronate-(1→4)-O-α-D-glucopyranosyl-(1→4)-O-3-O-ethyl-α-L-idopyranuronate-(1→4)-O-α-D-glucopyranoside (48 mg) was dissolved in dimethylformamide (1.4 ml) and sulfur trioxidetriethylamine complex (1.8 mmol) was added. After one night at 55° C. the mixture was cooled to room temperature and a mixture of sodium hydrogen carbonate (500 mg) and water (2 ml) was added. After evaporation the residue was layered on top of a Sephadex G25 column and eluted with water. The appropriate fractions were combined and freeze dried to give methyl O-3,4-di-O-methyl-2,6-di-O-sulfo-α-D-glucopyranosyl-(1→4)-O-2,3-di-O-methyl-β-D-glucopyranuronosyl-(1→4)-O-2,3,6-tri-O-sulfo-α-D-glucopyranosyl-(1→4)-O-3-O-ethyl-2-O-sulfo-α-L-idopyranuronosyl-(1→4)-O-2,3,6-tri-O-sulfo-α-D-glucopyranoside undecakis sodium salt. $[\alpha]_D^{20}$=+44.8 (c=1; water). Anomeric protons chemical shifts: 4.67; 5.14; 5.16; 5.53; and 5.55 ppm.

EXAMPLE 8

In a similar manner as described in Example 7 were prepared:

methyl O-2,3,4-tri-O-methyl-6-O-sulfo-α-D-glucopyranosyl-(1→4)-O-3-O-methyl-2-O-sulfo-β-D-glucopyranuronosyl-(1→4)-O-2,3,6-tri-O-sulfo-α-D-glucopyranosyl-(1→4)-O-3-O-ethyl-2-O-sulfo-α-L-idopyranuronosyl-(1→4)-O-2,3,6-tri-O-sulfo-α-D-glucopyranoside undecakis sodium salt. $[\alpha]_D^{20}$=+41.5 (c1; water). Anomeric protons chemical shifts: 4.76; 5.13; 5.15; 5.48; and 5.52 ppm.

methyl O-4-O-methyl-2,3,6-tri-O-sulfo-α-D-glucopyranosyl- (1→4)-O-2, 3-di-O-methyl-β-D-glucopyranuronosyl-(1→4)-O-2,3,6-tri-O-sulfo-α-D-glucopyranosyl-(1→4)-O-3-O-methyl-2-O-sulfo-α-L-idopyranuronosyl- (1→4)-O-2,3,6-tri-O-sulfo-α-D-glucopyranoside dodecakis sodium salt. $[\alpha]_D^{20}$=+43.1° (c=1; water). Anomeric protons chemical shifts: 4.67; 5.14; 5.16; 5.53; and 5.61 ppm.

EXAMPLE 9

In a similar manner as described in example 6 was prepared:
methyl O-3,4-di-O-sulfo-α-D-galactopyranosyl-(1→4)-O-2,3-di-O-methyl-b-D-glucopyranuronosyl-(1→4)-O-2,3,6-tri-O-sulfo-α-D-glucopyranosyl-(1→4)-O-3-O-methyl-2-O-sulfo-α-L-idopyranuronosyl-(1→4)-O-2,3,6-tri-O-sulfo-α-D-glucopyranoside, undecakis sodium salt. $[\alpha]_D^{20}$ =+48.8° (c=1.0; water). Anomeric protons chemical shifts: 4.60; 5.06; 5.06; 5.44; 5.52 ppm.

We claim:

1. A process for the preparation of a sulfated compound derived from a glycosaminoglycan, comprising coupling of protected monosaccharides to give protected disaccharides, which are optionally further coupled to tetra-, penta- or hexasaccharides; cleaving the protective groups partially or completely and sulfating free hydroxy groups; cleaving any remaining protective groups; and optionally converting the compound obtained into a pharmaceutically acceptable salt, wherein said compound produced by the above process comprises a saccharide unit having the formula I or II

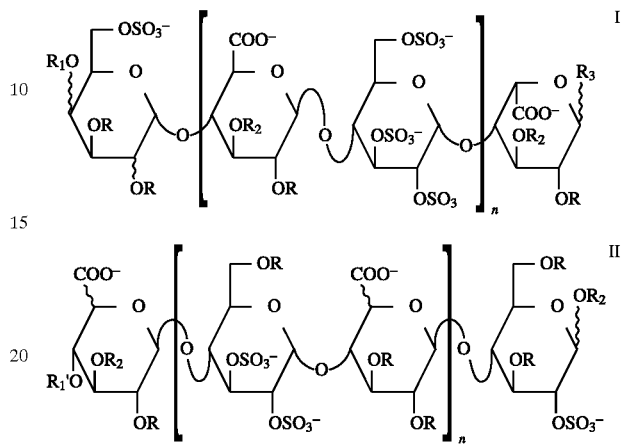

in which the twitched lines denote an α or β bond, each of the groups R are independently selected from the group consisting of alkyl and sulfate; n is 1 or 2; $R_1$ is selected from the group consisting of alkyl, aryl and aralkyl, and $R_1'$ has the same meaning as R, or is aryl, aralkyl or

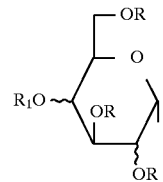

wherein R and $R_1$ have the previously given meanings; $R_2$ is alkyl; $R_3$ is alkoxy or

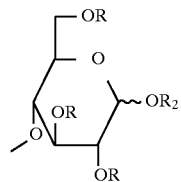

wherein the twitched line, R and $R_2$ have the previously given meanings, and the charged moieties are compensated by counterions.

* * * * *